United States Patent [19]

Buckle et al.

[11] 3,975,535

[45] Aug. 17, 1976

[54] ANTI-ALLERGIC-3-CARBOXY-ISOCOUMARIN COMPOSITIONS AND METHODS OF USE

[75] Inventors: Derek Richard Buckle, Redhill; Barrie Christian Charles Cantello, Horsham; Harry Smith, Maplehurst, near Horsham, all of England

[73] Assignee: Beecham Group Limited, England

[22] Filed: Sept. 30, 1974

[21] Appl. No.: 510,803

[30] Foreign Application Priority Data
Oct. 11, 1973  United Kingdom............... 47485/73

[52] U.S. Cl. ............................ 424/279; 260/295 F; 260/308 D; 260/347 R; 260/343.2 R; 424/263; 424/269; 424/275; 424/281
[51] Int. Cl.² ........................................ A61K 31/335
[58] Field of Search ..................... 424/279, 281; 260/343.2

[56] References Cited
UNITED STATES PATENTS

| | | | |
|---|---|---|---|
| 3,484,445 | 12/1969 | Lee et al. | 424/283 |
| 3,578,705 | 5/1971 | Wendler et al. | 260/343.2 R |
| 3,652,765 | 3/1972 | Ellis et al. | 424/283 |
| 3,733,338 | 5/1973 | Kimura et al. | 424/279 |
| 3,864,493 | 2/1975 | Cairns et al. | 424/283 |
| 3,879,544 | 4/1975 | Reisner et al. | 424/337 |
| 3,883,653 | 5/1975 | Barth | 424/251 |
| 3,885,038 | 5/1975 | Pfister et al. | 424/283 |

OTHER PUBLICATIONS

Physician's Desk Reference (PDR) 1974, pp. 760–761.

Molho et al. Chemical Abstracts 67:116789b (1967).

Aknin et al. Chemical Abstracts 67:73483c (1967).

*Primary Examiner*—Norman A. Drezin

[57] ABSTRACT

3-Carboxyisocoumarins, 2-thiaisocoumarins and related isocarbostyrils are useful anti-allergic agents. Several of these compounds are novel, and a process for their preparation is provided.

37 Claims, No Drawings

ANTI-ALLERGIC-3-CARBOXY-ISOCOUMARIN COMPOSITIONS AND METHODS OF USE

This invention relates to compositions which are useful in the inhibition of the effects of certain types of antigen-antibody reactions and are therefore of value in the prophylaxis and treatment of diseases associated with allergic or immunological reactions, e.g. certain types of asthma and hay fever, and also in the treatment of rhinitis. A number of the compounds comprising these compositions are novel, and a method for their preparation is provided.

We have discovered that a class of compounds of the general formula (I):

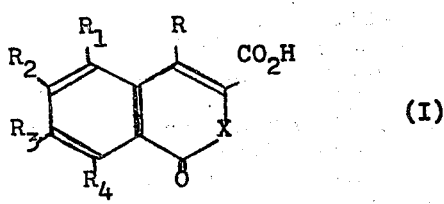

(I)

or a pharmaceutically acceptable salt thereof, in which formula X is O, S, or NH, R is hydrogen or an alkyl group; $R_1$, $R_2$, $R_3$, and $R_4$ are independently hydrogen or alkyl, alkoxy, aryl, aralkyl, heterocyclic, halogen, carboxylic acid groups or pharmaceutically acceptable salt, ester or amide derivatives of carboxylic acid groups, or acyloxy groups, and any two of $R_1$, $R_2$, $R_3$, and $R_4$ taken together may represent the residue of a substituted or unsubstituted carbocyclic or heterocyclic ring system, have useful activity in mammals in that they inhibit the effects of certain types of antigen-antibody reactions. In particular, they appear to inhibit the release of mediator substances, such as histamine, which are normally released after antigen-antibody combinations and which appear to mediate the allergic response.

A search of the chemical literature has revealed that not all of these compounds are novel. Below we list the compounds of the formula (I) which we have found in the literature, together with the appropriate reference:

Isocoumarin-3-carboxylic acid (ref 1)
4-Methylisocoumarin-3-carboxylic acid (ref 2)
6,7-Dimethoxyisocoumarin-3-carboxylic acid (ref 3)
Isocarbostyril-3-carboxylic acid (ref 4)
4-Methylisocarbostyril-3-carboxylic acid (ref 4)
6,7-Dimethyloxyisocarbostyril-3-carboxylic acid (ref 3)
2-Thiaisocoumarin-3-carboxylic acid (ref 4)
4-Methyl-2-thiaisocoumarin-3-carboxylic acid (ref 4)
6,7-Dimethoxy-2-thiaisocoumarin-3-carboxylic acid (ref 5)
7,8-Dimethoxyisocoumarin-3-carboxylic acid (ref 6)

REFERENCES

1. Boll. Sedute Acad. Gioenia Sci. Nat. Catania, (1960), 6, 625, F. Duro and P. Condorelli.
2. Boll. Sedute Acad. Gioenia Sci. Nat. Catania, (1960), 6, 606, F. Duro and P. Condorelli.
3. J. Ind. Chem. Soc., (1966), 43, 633. J. N. Chatterjea, H. C. Jha and B. K. Banerjee.
4. J. Chem. Soc., (1951), 1213. D. J. Dijksman, G. T. Newbold.
5. J. Chem. Soc., (1952), 4397, J. J. Brown, G. T. Newbold.
6. J. Gen. Chem. U.S.S.R. (1958) 28, 2547, L. I. Linevich.

Although the above compounds have been reported in the literature, no form of useful biological activity has been ascribed to them. Likewise there has been in the literature, no suggestion that such compounds are likely to possess any form of useful biological activity and in particular the discovery that they have anti-allergic activity has not been predicted in any way.

Accordingly, in its broadest aspect, the present invention provides a pharmaceutical composition having anti-allergy activity comprising a compound of the formula (I):

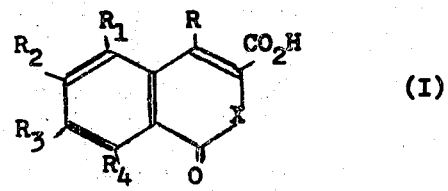

(I)

or a pharmaceutically acceptable salt thereof, together with one or more pharmaceutically acceptable carriers in which formula X is O, S or NH, R is hydrogen or an alkyl group; $R_1$, $R_2$, $R_3$ and $R_4$ are independently hydrogen or alkyl, alkoxy, aryl, aralkyl, heterocyclic, halogen, carboxylic acid groups or pharmaceutically acceptable salt, ester or amide derivatives of carboxylic acid groups, or acyloxy groups, and any two of $R_1$, $R_2$, $R_3$, and $R_4$ taken together may represent the residue of a substituted or unsubstituted carbocyclic or heterocyclic ring system, said composition being in a form suitable for administration to human beings.

The group R in compounds of the formula (I) is hydrogen or an alkyl group. Examples of suitable alkyl groups include methyl, ethyl, n- and iso-propyl, n- sec- or tert- butyl, cyclohexyl, cyclopentyl and cycloheptyl groups.

Examples of the groups $R_1$, $R_2$, $R_3$ and $R_4$ which may be present in the compounds of this invention include hydrogen, methyl, ethyl, n- and iso-propyl, n-, sec- and tert- butyl, cyclohexyl, methoxy, ethoxy, n- and isopropoxy, n-, sec- and tert- butoxy; phenyl; benzyl; pyridyl and tetrazolyl; fluoro, chloro, bromo and iodo; carboxyl, alkoxycarbonyl, acyloxymethoxycarbonyl, α-acyloxyethoxycarbonyl and acetoxy groups. In addition any two adjacent groups $R_1$ and $R_2$, $R_2$ and $R_3$, $R_3$ and $R_4$ taken together may represent the residue of a 1,2-phenylene or 1,2-cyclohexylene ring.

Preferably R, $R_1$ and $R_4$ are hydrogen and $R_2$ and $R_3$ are separately methoxy, ethoxy, n- propoxy or isopropoxy.

We have found that generally the most interesting compounds of the formula (I) are those wherein X is O or S.

Examples of specific compounds which can be incorporated in the compositions of the present invention include the following acids and their pharmaceutically acceptable salts:

Isocoumarin-3-carboxylic acid
4-Methylisocoumarin-3-carboxylic acid
8-Methylisocoumarin-3-carboxylic acid
4,8-Dimethylisocoumarin-3-carboxylic acid
7-Methoxyisocoumarin-3-carboxylic acid
7-Bromoisocoumarin-3-carboxylic acid
4,6,7-Trimethylisocoumarin-3-carboxylic acid monohydrate
6,7-Dimethoxyisocoumarin-3-carboxylic acid
Isocarbostyril-3-carboxylic acid
4-Methylisocarbostyril-3-carboxylic acid
6,7-Dimethoxyisocarbostyril-3-carboxylic acid
2-Thiaisocoumarin-3-carboxylic acid
4-Methyl-2-thiaisocoumarin-3-carboxylic acid
6,7-Dimethoxy-2-thiaisocoumarin-3-carboxylic acid
7,8-Dimethoxyisocoumarin-3-carboxylic acid Suitable pharmaceutically acceptable salts of compound (I) include metal salts such as sodium, potassium, aluminium or calcium salts, salts with organic bases such as amines or amino compounds.

The compositions of this invention may be presented as a microfine powder for insufflation, e.g. as a snuff or in capsules of hard gelatin. They may also be presented together with a sterile liquid carrier for injection. Some of the compounds of formula (I) are active when given by the oral route and in such cases the compositions of the invention may be in the form of tablets, capsules, pills or syrups. Preferably the compositions of this invention are presented in unit dosage form, or in a form in which the patient can administer to himself a single dose. If desired, a small amount of a bronchodilator compound such as isoprenaline may be incorporated in the compositions both to inhibit the cough response if the composition is insufflated and to provide immediate relief during an asthmatic attack. The effective dose of compound (I) depends on the particular compound chosen, but is generally in the range of from 0.1mg/kg/day to 100mg/kg/day.

The precise identity of the pharmaceutical carrier is not important and standard pharmaceutical practice may be followed.

Most of the compounds defined above with respect to formula (I) are believed to be novel. Accordingly the present invention includes within its scope such novel compounds, which are those of the formula (I), as herein before defined, and pharmaceutically acceptable salts thereof, excluding the following compounds and their pharmaceutically acceptable salts:

Isocoumarin-3-carboxylic acid
4-Methylisocoumarin-3-carboxylic acid
6,7-Dimethoxyisocoumarin-3-carboxylic acid
Isocarbostyril-3-carboxylic acid
4-Methylisocarbostyril-3-carboxylic acid
6,7-Dimethyloxyisocarbostyril-3-carboxylic acid
2-Thiaisocoumarin-3-carboxylic acid
4-Methyl-2-thiaisocoumarin-3-carboxylic acid
6,7-Dimethoxy-2-thiaisocoumarin-3-carboxylic acid
7,8-Dimethoxyisocoumarin-3-carboxylic acid The identities and preferred values of the groups R, $R_1$, $R_2$, $R_3$ and $R_4$ are as discussed earlier in the specification with respect to the pharmaceutical compositions of the invention, with the proviso that they may not be such that the resultant compound of the formula (I) is one of those known compounds specifically named in the preceding paragraph.

Specific examples of such novel compounds of the formula (I) include the following compounds and their pharmaceutically acceptable salts:

8-Methylisocoumarin-3-carboxylic acid
4,8-Dimethylisocoumarin-3-carboxylic acid
7-Methoxyisocoumarin-3-carboxylic acid
7-Bromoisocoumarin-3-carboxylic acid
4,6,7-Trimethylisocoumarin-3-carboxylic acid monohydrate The novel compounds of the formula (I) may be prepared by several different methods, depending on the nature of the group X.

When X is O, the compounds may be prepared by a process which comprises subjecting a compound of the formula (II):

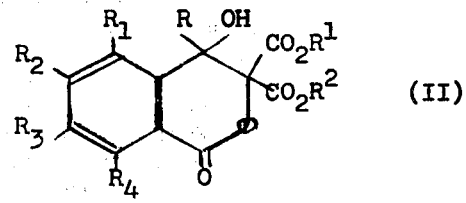
(II)

to acid hydrolysis wherein R, $R_1$, $R_2$, $R_3$ and $R_4$ are as defined in relation to formula (I) provided they are stable under the acid hydrolysis conditions chosen and $R^1$ and $R^2$ are separately an ester residue susceptible to acid hydrolysis and thereafter if desired converting the thus formed free carboxyl compound of the formula (I) to a pharmaceutically acceptable salt.

This reaction may be suitably carried out by refluxing the chosen compound of the formula (II) with a concentrated hydrochloric acid — acetic acid mixture.

The required intermediate of the formula (II) may be prepared by the reaction of the correspondingly substituted compound of the formula (III):

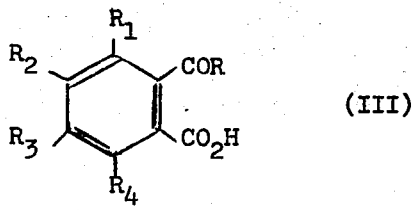

with diethyl bromomalonate under alkaline conditions.

When X is S and again when X is O, the novel compounds of the formula (I) may be prepared by a process which comprises reacting a compound of the formula (IV):

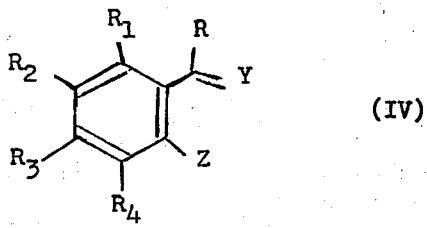

with an alkali; in formula (IV) R, $R_1$, $R_2$, $R_3$ and $R_4$ are as defined in relation to formula (I), Z is a carboxyl or esterified carboxyl group, and Y is either a group of the formula (V):

in which case X is S in the resultant compound of the formula (I), or a group of the formula (VI):

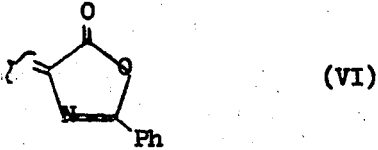

in which case X is O in the resultant compound of the formula (I); and thereafter if desired converting the thus formed salt of a compound of the formula (I) into an alternative salt or into the corresponding free carboxy compound.

A suitable alkali is sodium hydroxide.

When Z is an esterified carboxyl group, it is suitably a group —$CO_2R^4$, wherein $R^4$ is a $C_{1-6}$ alkyl group such as a methyl or ethyl group.

We have found that this reaction generally proceeds more satisfactorily when Y is a group of formula (V), yielding a compound of the formula (I) wherein X is S.

The intermediates of the formula (IV) may be prepared from the corresponding compound of the formula (III), as hereinbefore defined, or an alkyl ester thereof, by reacting the chosen compound of the formula (III) either with a compound of the formula (V)[1]:

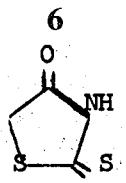

or with a compound of the formula (VI)[1]:

Reaction with a compound of the formula (V)[1] will of course yield an intermediate of the formula (IV) wherein Y is a group of formula (V). Similarly, reaction with a compound of the formula (VI)[1] will yield an intermediate of the formula (IV) wherein Y is a group of formula (VI).

When X is NH, the compounds of the formula (I) may be prepared by a process which comprises treating the corresponding compound of the formula (I) wherein X is O or S, with ammonia, and thereafter if desired forming an alternative salt or the corresponding free carboxy compound.

Suitably this process is carried out as an additional step in the two processes hereinbefore described for the preparation of the compounds of the formula (I) wherein X is O or S, which compounds are of course the intermediates in this reaction.

The following Examples illustrate the preparation of some of the compounds of the formula (I), and illustrate the biological activity of such compounds.

EXAMPLE 1

Isocoumarin-3-carboxylic acid

A mixture of 2-carboxybenzaldehyde (20.0g), diethyl bromomalonate (20.0g) and anhydrous potassium carbonate (20.0g) in ethyl methylketone (200ml.) was heated under reflux, with stirring, for 5 hours. The cooled mixture was evaporated to dryness and water (300ml.) added to the residue. After extraction with a mixture of ether-chloroform, the organic extracts were washed with water, dried and evaporated to dryness. The residual solid was heated under reflux with a mixture of concentrated hydrochloric acid (360ml.) — acetic acid (240ml.) for 2 hours. After cooling, the mixture was poured into iced water (1,200ml.). Filtration gave the product as a white solid, m.p. 241°-2° (lit mp. 239°-240°), (Found: C, 62.87; H, 3.39. $C_{10}H_6O_4$ requires C, 63.16; H 3.18).

EXAMPLE 2

4-Methylisocoumarin-3-carboxylic acid

A mixture of 2-acetylbenzoic acid (6.21g), diethyl bromomalonate (9.0g.) and potassium hydroxide (2.12g.) in ethanol (50ml.) was heated under reflux for 6 hours. The cooled mixture was evaporated to dryness, water (100ml.) added and extracted with ether. The combined ethereal extracts were washed with water, dried and evaporated to dryness. The residue was heated under reflux with a mixture of concentrated hydrochloric acid (160ml.) — acetic acid (100ml.) for two hours, cooled and poured into iced water (1 litre). Filtration gave the product as a white solid, mp. 250°-2°, (lit mp. 248°-9°) (Found: C, 64.59; H, 4.01. $C_{11}H_8O_4$ requires C, 64.70; H, 3.95).

EXAMPLE 3

8-Methylisocoumarin-3-carboxylic acid

8-Methylisocoumarin-3-carboxylic acid, mp. (EtOH-H$_2$O) 236°–7°, (Found: C, 64.66; H, 3.95. C$_{11}$H$_8$O$_4$ requires C, 64.70; H, 3.95), was prepared from 2-carboxy-3-methylbenzaldehyde by an analogous procedure to that described in Example 1.

EXAMPLE 4

4,8-Dimethylisocoumarin-3-carboxylic acid 4,8-Dimethylisocoumarin-3-carboxylic acid, mp. (EtOH- dilute HCl) 237°–9°, (Found: C, 66.33; H, 4.77. C$_{12}$H$_{10}$O$_4$ requires C, 66.05; H, 4.62) was prepared from 2-acetyl-6-methylbenzoic acid by an analogous procedure to that described in Example 2.

EXAMPLE 5

7-Methoxyisocoumarin-3-carboxylic acid

7-Methoxyisocoumarin-3-carboxylic acid, mp. (EtOH) 280°–3°, (Found: C, 60.11; H, 3.93. C$_{11}$H$_8$O$_5$ requires C, 60.00; H, 3.66) was prepared from 2-carboxy-4-methoxybenzaldehyde by an analogous procedure to that described in Example 1.

EXAMPLE 6

7-Bromoisocoumarin-3-carboxylic acid

7-Bromoisocoumarin-3-carboxylic acid, mp. (EtOH-H$_2$O) 320°–4°, (Found: C, 44.72; H, 1.86; Br. 29.41. C$_{10}$H$_5$BrO$_4$ requires C, 44.64; H, 1.87; Br. 29.70), was prepared from 4-bromo-2-carboxybenzaldehyde by an analogous procedure to that described in Example 1.

EXAMPLE 7

4,6,7-Trimethylisocoumarin-3-carboxylic acid monohydrate 4,6,7-Trimethylisocoumarin-3-carboxylic acid monohydrate, mp. (EtOH-H$_2$O) 241°, (Found: C, 62.27; H, 5.74 C$_{13}$H$_{12}$O$_4$. H$_2$O requires C, 62.39; H, 5.64) was prepared from 2-acetyl-4,5-dimethylbenzoic acid by an analogous procedure to that described in Example 2.

EXAMPLE 8

6,7-Dimethoxyisocoumarin-3-carboxylic acid 6,7-Dimethoxyisocoumarin-3-carboxylic acid, mp. 295°–7°, (lit mp. 295°–6°), (Found: C, 57.31; H, 4.03. C$_{12}$H$_{10}$O$_6$ requires C, 57.60; H, 4.03), was prepared from 2-carboxy-4,5-dimethoxybenzaldehyde (m-opianic acid) by an analogous procedure to that described in Example 1.

EXAMPLE 9

Isocarbostyril-3-carboxylic acid

Isocoumarin-3-carboxylic acid (1.40g.) was added to a solution of ammonia (d. 0.88, 10ml.) in ethanol (40ml.) at 0° and allowed to stand for 24 hours. After removal of solvent in vacuo, 6N hydrochloric acid (70ml.) was added and allowed to stand for 1 hour at 0°. Filtration gave the product as a white solid, mp. 327°–330° (lit mp. 326°–8°), (Found: C, 62.91; H, 3.69; N, 7.46. C$_{10}$H$_7$NO$_3$ requires C, 63.49; H, 3.73; N, 7.40).

EXAMPLE 10

4-Methylisocarbostyril-3-carboxylic acid

4-Methylisocarbostyril-3-carboxylic acid, mp. (HOAc) 336°–40° (d) (lit mp. 335°–6°), (Found: C, 65.18; H, 4.52; N, 6.41. C$_{11}$H$_9$NO$_3$ requires C, 65.02; H, 4.46; N, 6.89), was prepared from 4-methylisocoumarin-3-carboxylic acid by an analogous procedure to that described in Example 9.

EXAMPLE 11

6,7-Dimethoxyisocarbostyril-3-carboxylic acid 6,7-Dimethoxyisocarbostyril-3-carboxylic acid, mp. (HOAc) 316°–8° (lit mp. 313°–4°) was obtained as a hygroscopic solid, from the reaction of 6,7-dimethoxyisocoumarin-3-carboxylic acid with ammonia in ethanol at 50°, by an analogous procedure to that described in Example 9.

EXAMPLE 12

2-Thiaisocoumarin-3-carboxylic acid

A mixture of 5-(o-carboxybenzylidene) rhodanine (4.68g.) and sodium hydroxide (5.0g.) in water (40ml.) was heated under reflux for 30 minutes, cooled and poured into 5N hydrochloric acid (250ml.). Filtration and recrystallization from ethanol-water gave the product as a white solid, mp. 260.5°–261° (lit mp. 261°–3°), (Found: C, 58.10; H, 2.92; S, 15.41. C$_{10}$H$_8$SO$_3$ requires C, 58.24; H, 2.93; S, 15.55).

EXAMPLE 13

4-Methyl-2-thiaisocoumarin-3-carboxylic acid

4-Methyl-2-thiaisocoumarin-3-carboxylic acid mp. (EtOH-H$_2$O) 250.5°–251.5° (lit mp. 243°–5°), (Found: C, 60.40; H, 3.98; S, 14.80 C$_{11}$H$_8$SO$_3$ requires C, 59.99; H, 3.66; S, 14.56) was prepared from 5-(o-carboxy-α-methylbenzylidene) rhodanine by an analogous procedure to that described in Example 12.

EXAMPLE 14

6,7-Dimethoxy-2-thiaisocoumarin-3-carboxylic acid 6,7-Dimethoxy-2-thiaisocoumarin-3-carboxylic acid, mp. (EtOH) 300°–2°, (lit. mp. 306°–7°), (Found: C, 54.03; H, 3.80; S, 11.83, C$_{12}$H$_{10}$SO$_5$ requires C, 54.13; H, 3.79; S, 12.04) was prepared from 5-(2'-carboxy-4',5'-dimethoxybenzylidene) rhodanine by an analogous procedure to that described in Example 12.

EXAMPLE 15

7,8-Dimethoxyisocoumarin-3-carboxylic acid 7,8-Dimethoxyisocoumarin-3-carboxylic acid, mp. 262°–3° (lit. mp. 261°), (Found: C, 57.23; H, 3.91. C$_{12}$H$_{10}$O$_6$ requires C, 57.60; H, 4.03), was prepared from 2-carboxy-3,4-dimethoxybenzaldehyde (α-opianic acid) by an analogous procedure to that described in Example 1.

EXAMPLE 16

BIOLOGICAL RESULTS

All of the compounds prepared in the preceding Examples were submitted for biological testing. The test system was the Rat Passive Cutaneous Anaphylaxis (PCA) test described below in (ii).

i. Serum containing heat labile homocytotropic antibody was raised in rats by a method similar to that used by Mota. (I. Mota Immunology 1964, 7, 681).

Male Wistar rats of 250–300g. were injected intraperitoneally with 0.5 of *Bordatella pertussis* vaccine (containing 4 × 10$^{10}$ dead organism per ml) and subcutaneously with 0.5ml of an emulsion of 100mg. of ovalbumin in 2ml of saline and 3ml of incomplete Freunds' adjuvant. Rats were bled by cardiac puncture on day 18, the blood was pooled and separated and serum stored at −20° and thawed only once before use.

ii. The P.C.A. test was similar to that described by Ovary and Bier (A. Ovary and O. E. Bier, Proc. Soc. Exp. Biol. Med. 1952, 81, 584) and Goose and Blair (J. Goose and AMJ. N. Blair, Immunology 1969, 16, 769).

0.1ml of each of six twofold serial dilutions of the serum in 0.9% saline were injected intradermally into separate sites on the shaved dorsal surface of 250–350g. Wistar rats. 72 hours later the animals were challenged by i.v. injection of 0.3ml of 1% ovalbumin mixed with 0.1ml of a 5% solution of pontamine sky blue dye both in isotonic saline buffered with pH. 7.2 Sorenson buffer (P.B.S.). The rats were killed after 20 minutes and the diameter of the blue wheals at the antibody injection sites were measured. The starting dilution of the serum was adjusted so that there was no response, after challenge, at the site of injection of the highest dilution and a maximum response at the lowest dilution. Typically, six twofold serial dilutions of the serum from ¼ to 1/128 were used.

Compounds were tested for their ability to reduce the diameter of the wheals at the injection sites of dilutions of antibody which on all the controls have less than maximum response. Amounts of the compounds were administered to rats each amount to a test group of six animals at a specified time prior to intravenous challenge with ovalbumin. The diameters of the blue wheals which developed on the tests group of animals were compared with those on a control group of six animals treated in the same way as the test group, but which had not received the compound under test.

% Inhibition of P.C.A. = 100 (1 − a/b)

$a$ = The mean of the sum of the diameters of the wheals produced in the test group of animals at those antibody sites where all the control group of animals gave less than maximum response.

$b$ = The mean of the sum of diameters of the wheals produced in the control group of animals at those antibody sites where all the animals in the group gave less than maximum response.

The preferred method of administration was a solution of the test compound dissolved in pH 7.2 buffer and neutralised with sodium bicarbonate.

BIOLOGICAL RESULTS

| | Dose (mg/Kg) | Time (mins) | % Inhibition of PCA responses |
|---|---|---|---|
| EXAMPLE 1 | 25 | 0 | 29 |
| | 100 | 0 | 62 |
| | 25 | 30 | −13 |
| | 100 | 30 | 16 |
| EXAMPLE 2 | 25 | 0 | −3 |
| | 100 | 0 | 41 |
| | 25 | 30 | 0 |
| | 100 | 30 | 10 |
| EXAMPLE 3 | 25 | 0 | 44 |
| | 100 | 0 | 66 |
| | 25 | 30 | 15 |
| | 100 | 30 | 28 |
| EXAMPLE 4 | 25 | 0 | 10 |
| | 100 | 0 | 12 |
| | 25 | 30 | 8 |
| | 100 | 30 | 48 |
| EXAMPLE 5 | 25 | 0 | 9 |
| | 100 | 0 | 9 |
| | 25 | 60 | 4 |
| | 100 | 60 | 55 |

BIOLOGICAL RESULTS-continued

| | | Dose (mg/Kg) | Time (mins) | % Inhibition of PCA responses |
|---|---|---|---|---|
| EXAMPLE 6 | 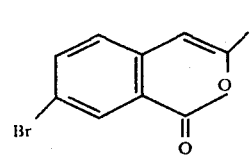 | 25<br>100<br>25<br>100 | 0<br>0<br>60<br>60 | 26<br>39<br>39<br>0 |
| EXAMPLE 7 | 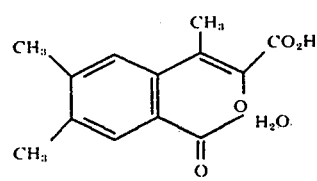 | 25<br>100<br>25<br>100 | 0<br>0<br>30<br>30 | 10<br>15<br>39<br>49 |
| EXAMPLE 8 | 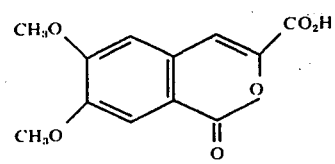 | 25<br>100<br>25<br>100 | 0<br>0<br>30<br>30 | 64<br>84<br>24<br>24 |
| EXAMPLE 9 | 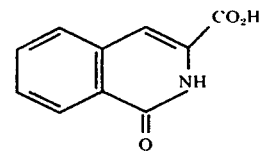 | 25<br>100<br>25<br>100 | 0<br>0<br>30<br>30 | 21<br>36<br>15<br>25 |
| EXAMPLE 10 | 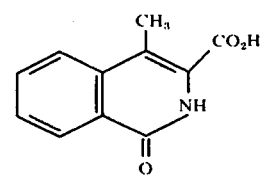 | 25<br>100<br>25<br>100 | 0<br>0<br>30<br>30 | 12<br>26<br>−13<br>21 |
| EXAMPLE 11 | 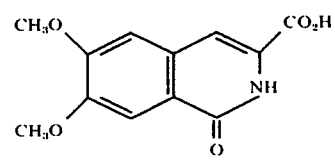 | 25<br>100<br>25<br>100 | 0<br>0<br>30<br>30 | 11<br>38<br>2<br>17 |
| EXAMPLE 12 | 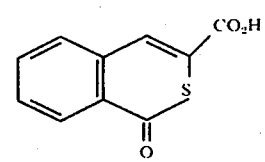 | 25<br>100<br>25<br>100 | 0<br>0<br>60<br>60 | 0<br>22<br>4<br>14 |
| EXAMPLE 13 | 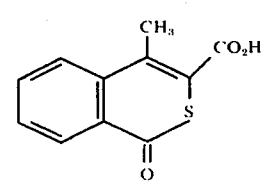 | 25<br>100<br>25<br>100 | 0<br>0<br>60<br>60 | −6<br>6<br>6<br>19 |

BIOLOGICAL RESULTS-continued

| | Dose (mg/Kg) | Time (mins) | % Inhibition of PCA responses |
|---|---|---|---|
| EXAMPLE 14 | 12.5 | 10 | 28 |
| | 25 | 10 | 47 |
| | 50 | 10 | 79 |
| | 100 | 10 | 87 |
| EXAMPLE 15 | 25 | 10 | 64 |
| | 100 | 10 | 63 |
| | 25 | 30 | 12 |
| | 100 | 30 | 29 |

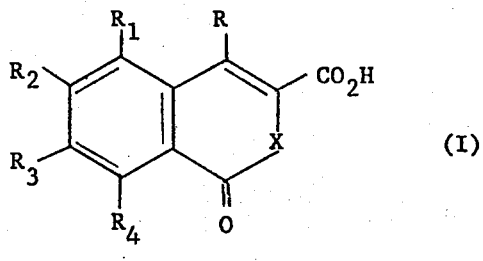

We claim:

1. A pharmaceutical composition in a form suitable for oral, parenteral or insufflation administration to humans which comprises a compound of the formula (I)

$$\text{(I)}$$

or a pharmaceutically acceptable salt thereof or hydrate thereof, wherein X is O, R is hydrogen, lower alkyl, cyclopentyl, cyclohexyl or cycloheptyl; $R_1$, $R_2$, $R_3$ and $R_4$ are each hydrogen, lower alkyl, lower alkoxy, cyclohexyl, phenyl, benzyl, halogen, carboxyl, lower alkoxycarbonyl, lower alkanoyloxymethoxycarbonyl, lower α-alkanoyloxyethoxycarbonyl or acetoxy, or $R_1$ and $R_2$, $R_2$ and $R_3$ or $R_3$ and $R_4$ taken together with the carbon atoms to which they are attached form a 1,2-phenylene or 1,2-cyclohexylene ring, in an amount sufficient to be effective for the prophylaxis of asthma, hayfever, or rhinitis in combination with a pharmaceutically acceptable non-toxic inert diluent or carrier suitable for said administration form.

2. A pharmaceutical composition according to claim 1, wherein R is hydrogen, methyl, ethyl, n- or iso-propyl, n-, sec- or tert-butyl, cyclopentyl, cyclohexyl or cycloheptyl; $R_1$, $R_2$, $R_3$ and $R_4$ are each methyl, ethyl, n- or iso-propyl, n-, sec- or tert- butyl, cyclohexyl, methoxy, ethoxy, n- or iso- propoxy, n-, sec- or tert- butoxy, phenyl, benzyl, fluoro, chloro, bromo, iodo, carboxyl, lower alkoxycarbonyl, lower alkanoyloxymethoxycarbonyl, lower α-alkanoyloxyethoxycarbonyl or acetoxy, or $R_1$ and $R_2$, $R_2$ and $R_3$, or $R_3$ and $R_4$ together with the carbon atoms to which they are attached form a 1,2-phenylene or 1,2-cyclohexylene ring.

3. A pharmaceutical composition according to claim 1, wherein R, $R_1$ and $R_4$ are each hydrogen, and $R_2$ and $R_3$ are each methoxy, ethoxy, n-propoxy or isopropoxy.

4. A pharmaceutical composition according to claim 1, wherein the compound is isocoumarin-3-carboxylic acid, or a pharmaceutically acceptable salt thereof.

5. A pharmaceutical composition according to claim 1 wherein the compound is 8-methylisocoumarin-3-carboxylic acid, or a pharmaceutically acceptable salt thereof.

6. A pharmaceutical composition according to claim 1, wherein the compound is 6,7-dimethoxyisocoumarin-3-carboxylic acid, or a pharmaceutically acceptable salt thereof.

7. A pharmaceutical composition according to claim 1, wherein the compound is 7,8-dimethoxyisocoumarin-3-carboxylic acid, or a pharmaceutically acceptable salt thereof.

8. A pharmaceutical composition according to claim 1 which is in the form of a microfine powder for insufflation.

9. A pharmaceutical composition according to claim 8 which additionally contains a small amount of bronchodilator.

10. A pharmaceutical composition according to claim 9 wherein the bronchodilator is isoprenaline.

11. A pharmaceutical composition according to claim 1 wherein the pharmaceutically acceptable diluent or carrier is a sterile liquid suitable for injection.

12. A pharmaceutical composition according to claim 1 in the form of a pill, a tablet, or a capsule or a powder which is suitable for mixing with water to form a syrup.

13. A pharmaceutical composition according to claim 1 wherein $R_1$, $R_2$, $R_3$ and $R_4$ are each hydrogen, methyl, methoxy or bromo.

14. A pharmaceutical composition according to claim 1 wherein the pharmaceutically acceptable salt is a metal salt or an amine or amino salt.

15. A pharmaceutical composition according to claim 1 wherein the compound is in monohydrate form.

16. A pharmaceutical composition according to claim 1 wherein the compound is 4-methylisocoumarin-3-carboxylic acid.

17. A pharmaceutical composition according to claim 1 wherein the compound is 4,8-dimethylisocoumarin-3-carboxylic acid.

18. A pharmaceutical composition according to claim 1 wherein the compound is 7-methoxyisocoumarin-3-carboxylic acid.

19. A pharmaceutical composition according to claim 1 wherein the compound is 7-bromoisocoumarin-3-carboxylic acid.

20. A pharmaceutical composition according to claim 1 wherein the compound is 4,6,7-trimethylisocoumarin-3-carboxylic acid monohydrate.

21. A method for the prophylaxis of asthma, hayfever and rhinitis in humans which comprises administering to a human in need thereof orally, parenterally or by insufflation a compound of the formula (I):

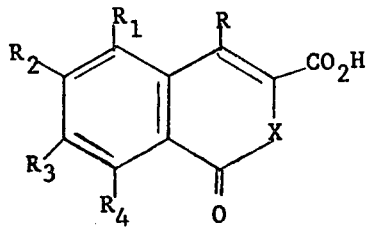

(I)

or a pharmaceutically acceptable salt thereof or hydrate thereof, wherein X is O, R is hydrogen, lower alkyl, cyclopentyl, cyclohexyl or cycloheptyl; $R_1$, $R_2$, $R_3$ and $R_4$ are each hydrogen, lower alkyl, lower alkoxy, cyclohexyl, phenyl, benzyl, halogen, carboxyl lower alkoxycarbonyl, lower alkanoyloxmethoxycarbonyl, lower α-alkanoyloxyethoxycarbonyl or acetoxy, or $R_1$ and $R_2$, $R_2$ and $R_3$ or $R_3$ and $R_4$ taken together with the carbon atoms to which they are attached form a 1,2-phenylene or 1,2-cyclohexylene ring in an amount sufficient to be effective for the prophylaxis of asthma, hayfever or rhinitis, in combination with a pharmaceutically acceptable non-toxic diluent or carrier suitable for said administration form.

22. A method according to claim 18 wherein R is hydrogen, methyl, ethyl, n- or iso-propyl, n-, sec- or tert-butyl, cyclopentyl, cyclohexyl or cycloheptyl; $R_1$, $R_2$, $R_3$ and $R_4$ are each methyl, ethyl, n- or iso-propyl, n-, sec- or tert-butyl, cyclohexyl, methoxy, ethoxy, n- or iso-propoxy, n-, sec- or tert-butoxy, phenyl, benzyl, fluoro, chloro, bromo, iodo, carboxyl, lower alkoxycarbonyl, lower alkanoyloxymethoxycarbonyl, lower α-alkanoyloxyethoxycarbonyl or acetoxy, or $R_1$ and $R_2$, $R_2$ and $R_3$, or $R_3$ and $R_4$ together with the carbon atoms to which they are attached form a 1,2-phenylene or 1,2-cyclohexylene ring.

23. A method according to claim 18 wherein R, $R_1$ and $R_4$ are each hydrogen, and $R_2$ and $R_3$ are each methoxy, ethoxy, n- propoxy or iso- propoxy.

24. A method according to claim 18 wherein $R_1$, $R_2$, $R_3$ and $R_4$ are each hydrogen, methyl, methoxy or bromo.

25. A method according to claim 18 wherein the pharmaceutically acceptable salt is a metal salt or an amine or amino salt.

26. A method according to claim 18 wherein the compound is in monohydrate form.

27. A method according to claim 18 wherein the compound and the diluent or carrier are in the form of a microfine powder and the administration is by insufflation.

28. A method according to claim 18 which comprises administering the compound and the diluent or carrier in combination with a small amount of a brochodilator by insufflation.

29. A method according to claim 25 wherein the bronchodilator is isoprenaline.

30. A method according to claim 18 wherein the diluent or carrier is a sterile liquid suitable for injection and the administration is by injection.

31. A method according to claim 18 wherein the compound and the diluent or carrier are formed into a pill, tablet or capsule or a powder which is suitable for mixing with water to form a syrup and the administration is oral.

32. A method according to claim 18 wherein the compound is isocoumarin-3-carboxylic acid or a pharmaceutically acceptable salt thereof.

33. A method according to claim 18 wherein the compound is 4-methylisocoumarin-3-carboxylic acid or a pharmaceutically acceptable salt thereof.

34. A method according to claim 18 wherein the compound is 4,8-dimethylisocoumarin-3-carboxylic acid, or a pharmaceutically acceptable salt thereof.

35. A method according to claim 18 wherein the compound is 7-methoxyisocoumarin-3-carboxylic acid, or a pharmaceutically acceptable salt thereof.

36. A method according to claim 18 wherein the compound is 7-bromoisocoumarin-3-carboxylic acid, or a pharmaceutically acceptable salt thereof.

37. A method according to claim 18 wherein the compound is 4,6,7-trimethylisocoumarin-3-carboxylic acid monohydrate, or a pharmaceutically acceptable salt thereof.

* * * * *

UNITED STATES PATENT AND TRADEMARK OFFICE
CERTIFICATE OF CORRECTION

PATENT NO. : 3,975,535

DATED : August 17, 1976

INVENTOR(S) : Derek Richard Buckle, Barrie Christian Charles Cantello and Harry Smith It is certified that error appears in the above-identified patent and that said Letters Patent are hereby corrected as shown below:

In claim 2, column 13, line 56, following "each" insert -- hydrogen, --.

In claim 22, column 15, line 39, following "each" insert -- hydrogen, --.

Signed and Sealed this

Tenth Day of May 1977

[SEAL]

Attest:

RUTH C. MASON
*Attesting Officer*

C. MARSHALL DANN
*Commissioner of Patents and Trademarks*